US008088946B2

(12) United States Patent
Himeno et al.

(10) Patent No.: US 8,088,946 B2
(45) Date of Patent: *Jan. 3, 2012

(54) METHOD FOR MANUFACTURING PALLADIUM-CONTAINING CATALYST

(75) Inventors: Yoshiyuki Himeno, Hiroshima (JP); Wataru Ninomiya, Hiroshima (JP); Ken Ooyachi, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 936 days.

This patent is subject to a terminal disclaimer.

(21) Appl. No.: 11/719,461

(22) PCT Filed: Nov. 14, 2005

(86) PCT No.: PCT/JP2005/020835
§ 371 (c)(1),
(2), (4) Date: Apr. 2, 2008

(87) PCT Pub. No.: WO2006/054515
PCT Pub. Date: May 26, 2006

(65) Prior Publication Data
US 2008/0306298 A1 Dec. 11, 2008

(30) Foreign Application Priority Data

Nov. 17, 2004 (JP) ................. 2004-333204
Oct. 5, 2005 (JP) ................. 2005-292393

(51) Int. Cl.
*C07C 51/16* (2006.01)
(52) U.S. Cl. ......... 562/534; 562/533; 562/545; 562/546
(58) Field of Classification Search ................. None
See application file for complete search history.

(56) References Cited

U.S. PATENT DOCUMENTS

2007/0142666 A1 6/2007 Himeno et al.

FOREIGN PATENT DOCUMENTS

| CN | 1165111 A | 11/1997 |
| EP | 0145467 A2 | 12/1984 |
| EP | 0 145 469 A2 | 6/1985 |
| EP | 0145469 | * 6/1985 |
| JP | 51 1389 | 1/1976 |
| JP | 60 139341 | 7/1985 |
| JP | 2000 202287 | 7/2000 |
| JP | 2004-141863 | 5/2004 |
| JP | 2004 519326 | 7/2004 |
| KP | 2004141863 | * 5/2004 |
| WO | WO 02/083299 A2 | 10/2002 |

OTHER PUBLICATIONS

Machine translation of JP 2004141863.*
Toshihiko Kubo, et al., "Zeolite Y Jo No Palladium No Bunsan Jotai To Shokubai Kassei (Dispersion State of Palladium on Zeolite Y and Catalytic Activities)", Journal of the Chemical Society of Japan, vol. 8, No. 7, pp. 1199-1203, 1974. (with English abstract and partial English translation).
U.S. Appl. No. 11/628,215, filed Dec. 1, 2006, Kawato et al.
U.S. Appl. No. 11/628,214, filed Dec. 1, 2006, Ninomiya et al.
U.S. Appl. No. 12/159,396, filed Jun. 27, 2008, Himeno et al.
Toshihiko Kubo et al., "A State of Palladium Dispersed on Zeolite Y, and Its Catalytic Activity,", Journal of the Chemical Society of Japan, vol. 8, No. 7, pp. 1199-1203 (submitting full English translation only), 1974.

* cited by examiner

Primary Examiner — Karl J Puttlitz
(74) Attorney, Agent, or Firm — Oblon, Spivak, McClelland, Maier & Neustadt, L.L.P.

(57) ABSTRACT

The present invention provides: a palladium-containing supported catalyst which is used for producing an α,β-unsaturated carboxylic acid from an olefin or an α,β-unsaturated aldehyde in high selectivity; a method for manufacturing the catalyst; and a method for producing an α,β-unsaturated carboxylic acid in high selectivity. In particular, the present invention resides in a method for manufacturing a palladium-containing supported catalyst for producing an α,β-unsaturated carboxylic acid from an olefin or an α,β-unsaturated aldehyde, comprising the step of reducing palladium oxide contained in a catalyst precursor wherein at least the palladium oxide is supported on a carrier. By using such a palladium-containing supported catalyst, an α,β-unsaturated carboxylic acid is produced through liquid-phase oxidation of an olefin or an α,β-unsaturated aldehyde with molecular oxygen.

20 Claims, No Drawings

METHOD FOR MANUFACTURING PALLADIUM-CONTAINING CATALYST

CROSS REFERENCE TO RELATED APPLICATION

This application is a 371 of PCT/JP05/020835, filed on Nov. 14, 2005, and claims priority to the following Japanese Patent Applications: 2004-333204, filed on Nov. 17, 2004; and 2005-292393, filed on Oct. 5, 2005.

TECHNICAL FIELD

The present invention relates to a method for manufacturing a palladium-containing supported catalyst for producing an α,β-unsaturated carboxylic acid from an olefin or an α,β-unsaturated aldehyde. Further, the present invention relates to a method for producing an α,β-unsaturated carboxylic acid.

BACKGROUND ART

As a palladium-containing supported catalyst for producing an α,β-unsaturated carboxylic acid through liquid-phase oxidation of an olefin with molecular oxygen, there has been proposed in, for example, International Publication No. WO 2002/083,299 A1, a supported catalyst of palladium metal which is formed by reducing a palladium salt with a reducing agent. Further, in Japanese Patent Application Laid-Open No 2000-202,287, a palladium catalyst for hydrogen addition reaction manufactured by supporting a dinitrodiammine palladium solution on an alumina carrier followed by reduction is described.

DISCLOSURE OF INVENTION

Problem to be Solved by the Invention

However, there is no description or suggestion of using the palladium catalyst for hydrogen addition reaction described in Japanese Patent Application Laid-Open No. 2000-202,287 to an oxidation reaction. Further, the selectivity to an α,β-unsaturated carboxylic acid of the catalyst manufactured by the method described in International Publication No. WO 2002/083,299 A1 is not sufficient yet and a catalyst for producing an α,β-unsaturated carboxylic acid with higher selectivity has been desired.

Therefore, it is an object of the present invention to provide a palladium-containing supported catalyst for producing an α,β-unsaturated carboxylic acid from an olefin or an α,β-unsaturated aldehyde in high selectivity. It is a further object of the present invention to provide a method for producing the catalyst. It is still another object of the present invention to provide a method for producing an α,β-unsaturated carboxylic acid in high selectivity.

Means for Solving the Problem

The present invention resides in a method for manufacturing a palladium-containing supported catalyst for producing an α,β-unsaturated carboxylic acid from an olefin or an α,β-unsaturated aldehyde, comprising the step of reducing palladium oxide contained in a catalyst precursor wherein the palladium oxide is in a state of being supported on a carrier.

It is preferable that the catalyst precursor be the one which is prepared by a method comprising the steps of: supporting a palladium salt on the carrier; and forming the catalyst precursor in which at least a part of the palladium salt supported on the carrier has been changed into palladium oxide by heat treatment of the carrier on which the palladium salt had been supported.

It is preferable to perform the foregoing heat treatment at the thermal decomposition temperature of the foregoing palladium salt or higher.

Besides, the present invention resides in a palladium-containing supported catalyst manufactured by the foregoing method.

Further, the present invention resides in a method for producing an α,β-unsaturated carboxylic acid through liquid-phase oxidation of an olefin or an α,β-unsaturated aldehyde with molecular oxygen by using the foregoing palladium-containing supported catalyst.

Effect of the Invention

According to the method for manufacturing the palladium-containing supported catalyst of the present invention, the palladium-containing supported catalyst which can produce an α,β-unsaturated carboxylic acid in high selectivity can be produced in the case that the α,β-unsaturated carboxylic acid is produced from an olefin or an α,β-unsaturated aldehyde.

Besides, according to the palladium-containing supported catalyst of the present invention, an α,β-unsaturated carboxylic acid can be produced in high selectivity in the case that the α,β-unsaturated carboxylic acid is produced from an olefin or an α,β-unsaturated aldehyde.

Further, according to the method for producing an α,β-unsaturated carboxylic acid through liquid-phase oxidation of an olefin or an α,β-unsaturated aldehyde with molecular oxygen by using the palladium-containing supported catalyst of the present invention, an α,β-unsaturated carboxylic acid can be produced in high selectivity.

BEST MODE FOR CARRYING OUT THE INVENTION

The method for manufacturing the palladium-containing supported catalyst of the present invention comprises the step of reducing palladium oxide contained in a catalyst precursor wherein the palladium oxide is in a state of being supported on a carrier. An α,β-unsaturated carboxylic acid can be produced in high selectivity from an olefin or an α,β-unsaturated aldehyde by using the palladium-containing catalyst obtained by this method for manufacturing the palladium-containing supported catalyst. As a factor of being able to produce an α,β-unsaturated carboxylic acid in high selectivity it is presumed that a catalyst composed of palladium atoms in highly dispersed state can be manufactured because coagulation and particle growth of palladium metal produced in the reduction step can be suppressed owing to a stronger interaction between palladium oxide and the carrier than that in the case of a conventional palladium salt.

The facts that palladium oxide is supported on the carrier and palladium metal is supported on the finally obtained palladium-containing supported catalyst, and the physical properties thereof can be confirmed by XRD measurement, XPS measurement, TEM observation, and the like. For example, formation of palladium oxide and palladium metal can be confirmed by checking three strong peaks in the XRD measurement.

(Peaks to be checked)
Palladium oxide d value: 2.64, 1.68, 2.67
Palladium metal d value: 2.25, 1.95, 1.38

The palladium-containing supported catalyst of the present invention is a supported catalyst in which elements composing the catalyst are supported on a carrier, and manufactured by the foregoing method.

As the carrier, it is not particularly limited as long as it can support palladium oxide. In the present invention, a method in which a palladium salt is supported on a carrier, at first, and then the resultant carrier is subjected to heat treatment is preferable as an embodiment, as mentioned later, and a carrier of inorganic oxide which does not burn or change in quality by the conditions of the heat treatment is preferable. For example, silica, alumina, silica-alumina, magnesia, calcia, titania, zirconia, and the like can be listed. Among them, silica, titania and zirconia are preferable. The carrier can be used alone or in combination of two or more kinds.

Preferable specific surface area of the carrier cannot be absolutely fixed because it is variable depending on a kind of carrier, and the like, and in the case of silica, 50 $m^2/g$ or more is preferable and 100 $m^2/g$ or more is more preferable. Further, it is preferably 1,500 $m^2/g$ or less and more preferably 1,000 $m^2/g$ or less. As the specific surface area of the carrier becomes smaller, a catalyst in which the effective component is supported more on its surface can be produced, and as the specific surface area of the carrier becomes larger, a catalyst in which the effective component is supported more can be produced.

A catalyst precursor in which at least palladium oxide is supported on the foregoing carrier is prepared. The catalyst precursor may be prepared by a method in which the carrier and palladium oxide are dispersed in a solvent, at first, and then the solvent is evaporated, however, it is preferable to adopt a method in which a palladium salt is previously supported on the carrier and the resultant carrier is subjected to heat treatment to obtain a good dispersion of palladium atoms in the finally obtained palladium-containing supported catalyst.

As the method for supporting the palladium salt on the carrier, a method of soaking the carrier in the palladium salt-dissolved liquid followed by evaporating the solvent or a method of absorbing the palladium salt-dissolved liquid, the amount of which is equivalent to the amount of pore volume of the carrier, into the carrier followed by evaporating the solvent, namely a pore-filling method, is preferable. As the solvent that dissolves the palladium salt, it is not particularly limited as long as it can dissolve the palladium salt.

At least a part of the palladium salt changes into palladium oxide through thermal decomposition by being subjected to heat treatment in a state of being supported on a carrier. It is preferable that the temperature of the heat treatment be a thermal decomposition temperature of the palladium salt or higher. Further, it is preferably 800° C. or lower and more preferably 700° C. or lower. The method for raising temperature to the predetermined temperature of the heat treatment is not particularly limited, however, the speed of raising temperature is preferably 1 to 10° C./min to obtain a good dispersion of palladium atoms in the palladium-containing supported catalyst. The holding time after the predetermined temperature of the heat treatment is attained is not particularly limited as long as it is enough to decompose the palladium salt however, it is preferably 1 to 12 hours.

Further, in the present invention, it is preferable that the heat treatment be carried out at a thermal decomposition temperature of the palladium salt or higher to change the palladium salt into palladium oxide. By doing so, coagulation and particle growth of palladium particles can be suppressed, and consequently, dispersibility of the palladium particles is improved to be able to produce an α,β-unsaturated carboxylic acid in higher selectivity from an olefin or an α,β-unsaturated aldehyde.

In the present invention, it is preferable that a palladium salt with the thermal decomposition temperature of 400° C. or lower be adopted and supported on a carrier. The thermal decomposition temperature of the palladium salt is more preferably 300° C. or lower and it is particularly preferably 200° C. or lower. As the decomposition temperature of the palladium salt becomes lower, the calorific value becomes smaller. Therefore, by using the palladium salt with the thermal decomposition temperature of 200° C. or lower, in particular, it is possible to make the calorific value small to suppress the coagulation and particle growth of the palladium particles even when a thickness of a carrier layer on which the palladium salt is supported is large at the time of the heat treatment. Consequently, an α,β-unsaturated carboxylic acid can be produced in higher selectivity. There is a great merit in the case of scaleup that a catalyst with high selectivity can be manufactured even when the thickness of the carrier layer is large because it is usually inevitable in a catalyst preparation under the industrial scale that the thickness of the carrier layer, the palladium salt being supported on the carrier, at the time of the heat treatment becomes large owing to the relation between an amount of the catalyst and a scale of a calcining device, and the like.

Namely, it is illustrated as a particularly preferable embodiment to use a catalyst precursor in which at least a part of the palladium salt supported on the carrier has been changed into palladium oxide by supporting a palladium salt with the thermal decomposition temperature of 400° C. or lower on the carrier and subjecting the carrier on which the palladium salt is supported to the heat treatment at a thermal decomposition temperature of the palladium salt or higher.

As the palladium salt to be used, for example, palladium(II) chloride (thermal decomposition temperature: 650° C.), palladium(II) acetate (thermal to decomposition temperature: 230° C.), palladium(II) nitrate (thermal decomposition temperature: 120° C.), tetraamminepalladium(II) nitrate (thermal decomposition temperature: 220° C.) and bis-(acetylacetonato)palladium(II) (thermal decomposition temperature: 210° C.) can be listed. Among them, palladium(II) acetate, palladium(II) nitrate, tetraamminepalladium(II) nitrate and bis-(acetylacetonato)palladium(II) are preferable. The palladium salt can be used alone or in combination of two or more kinds.

Now, the thermal decomposition temperature of the palladium salt can be measured with thermogravimetry. The thermal decomposition temperature of the palladium salt was defined as a temperature at which 10% of the weight of the palladium salt was reduced by raising the temperature of the palladium salt from a room temperature at a rate of 5.0° C./min in air low by using thermogravimeter (trade name: TGA-50, manufactured by Shimadzu Corporation).

By the foregoing heat treatment, a catalyst precursor in which at least a part of the palladium salt supported on the carrier has been changed into palladium oxide by decomposition can be obtained. Further, in the present invention, the palladium oxide included in the catalyst precursor obtained by the foregoing heat treatment is reduced. Concretely the palladium oxide supported on the carrier is reduced by a reducing agent to obtain palladium metal. When a palladium salt also exists on the carrier of the catalyst precursor, the palladium salt is also reduced at the same time to become palladium metal.

The reducing agent to be used is not particularly limited. For example, hydrazine, formaldehyde, sodium boron hydride, hydrogen, formic acid, formate, ethylene, propylene, 1-butene, 2-butene, isobutylene, 1,3-butadiene, 1-heptene, 2-heptene, 1-hexene, 2-hexene, cyclohexene, allylalcohol, methallyl alcohol, acrolein, and methacrolein can be listed. The reducing agent can be used in combination of two or more kinds. In the case of gas-phase reduction, hydrogen is preferable as the reducing agent. Further, in the case of liquid-phase reaction, hydrazine, formaldehyde, formic acid, and formate are preferable as the reducing agent.

As the solvent to be used at the time of reduction in a liquid phase, water is preferable, however, an organic solvent like alcohols such as ethanol, 1-propanol, 2-propanol, n-butanol and t-butanol; ketones such as acetone, methyl ethyl ketone, methyl isobutyl ketone and cyclohexanone; organic acids such as acetic acid, n-valeric acid and isovaleric acid; hydrocarbons such as heptane, hexane, and cyclohexane can be used alone or in combination of two or more kinds depending on dispersibility of the carrier. A mixed solvent of these and water can also be used.

In the case that the reducing agent is a gas, it is preferable to carry out the reduction in a pressure device such as an autoclave to increase solubility of the gas to the solution. On this occasion, the inside of the pressure device is pressurized by the reducing agent. This pressure is preferably 0.1 to 1.0 MPa (gauge pressure; hereinafter, pressure is expressed in gauge pressure).

Besides, in the case that the reducing agent is a liquid, a device for reducing palladium oxide is not particularly limited and the reduction can be carried out by adding a reducing agent in the solution. In this case, the amount of use of the reducing agent is not particularly limited, however, it is preferably 1 to 100 moles to 1 mole of palladium oxide.

The reducing temperature and the reducing time are variable depending on the reducing agent, however, the reducing temperature is preferably −5 to 150° C. and more preferably 15 to 80° C. The reducing time is preferably 0.1 to 4 hours, more preferably 0.25 to 3 hours, and further preferably 0.5 to 2 hours.

After the reduction, a palladium-containing supported catalyst in which palladium metal is supported on the carrier is separated. The method for separating this catalyst is not particularly limited, however, for example, filtration and centrifugation can be used. The palladium-containing supported catalyst thus separated is properly dried. The method for drying is not particularly limited and various methods can be used.

Now, the palladium-containing supported catalyst of the present invention can contain metal components other than palladium. As the metal components other than palladium, for example, ruthenium, rhodium, silver, osmium, iridium, platinum, gold, copper, antimony, tellurium, lead, and bismuth can be listed. It is preferable that the content of palladium metal among the metals contained in the palladium-containing supported catalyst be 50% by mass or more from the viewpoint of realizing a high catalyst activity. The palladium-containing supported catalyst containing these metal components can be obtained by supporting metal compounds such as metal salts and oxides corresponding to these metals on the carrier and subjecting the resultant system to the foregoing reduction, if necessary. In this case, the method for supporting the metal compounds is not particularly limited and can be the same as that in the case of supporting a palladium salt. Further, the metal compounds can be supported before the palladium salt is supported, after the palladium salt is supported or at the same time that the palladium salt is supported.

The loading ratio of the metal components including palladium to the carrier is preferably 0.1 to 40% by mass to the carrier before the metal components are supported, more preferably 0.05 to 30% by mass, further preferably 1 to 20% by mass.

Next, a method for producing an α,β-unsaturated carboxylic acid through liquid-phase oxidation of an olefin or an α,β-unsaturated aldehyde with molecular oxygen by using the palladium-containing supported catalyst of the present invention will be explained.

As the olefin which is the raw material of the reaction, for example, propylene, isobutylene and 2-butene can be listed. Further, as the α,β-unsaturated aldehyde which is the raw material of the reaction, for example, acrolein, methacrolein, crotonaldehyde (β-methylacrolein and cinnamaldehyde (β-phenylacrolein) can be listed.

In the case that the raw material is an olefin, the α,β-unsaturated carboxylic acid to be produced is the one having the same carbon skeleton as the raw olefin has. In the case that the raw material is an α,β-unsaturated aldehyde, the α,β-unsaturated carboxylic acid to be produced is the one in which the aldehyde group of the α,β-unsaturated aldehyde has changed into the carboxyl group.

The method for producing an α,β-unsaturated carboxylic acid of the present invention is suitable for a liquid-phase oxidation of propylene or acrolein to acrylic acid, or a liquid-phase oxidation of isobutylene or methacrolein to methacrylic acid.

The olefin or the α,β-unsaturated aldehyde which is the raw material may contain a little amount of at least one of saturated hydrocarbons and lower saturated aldehydes as impurities.

The source of molecular oxygen to be used in the liquid-phase oxidation is preferably air because it is economical, however, pure oxygen or a mixed gas of pure oxygen and air can also be used, and if necessary, a diluted mixed gas in which air or pure oxygen is diluted with nitrogen, carbon dioxide or water vapor can also be used.

The solvent to be used in the liquid-phase oxidation is not particularly limited. For example, water; alcohols such as tertiary butanol and cyclohexanol; ketones such as acetone, methyl ethyl ketone and methyl isobutyl ketone; organic acids such as acetic acid, propionic acid, n-butyric acid, isobutyric acid, n-valeric acid and isovaleric acid; organic acid esters such as ethyl acetate and methyl propionate; hydrocarbons such as hexane, cyclohexane and toluene can be used. Among them organic acids having 2 to 6 carbon atoms, ketones having 3 to 6 carbon atoms and tertiary butanol are preferable. These solvents can be used alone or in combination of two or more kinds. Further, in the case of using at least one kind selected from the group consisting of alcohols, ketones, organic acids and organic acid esters, it is preferable to use it as a mixed solvent with water. In this case, the amount of water is not particularly limited, however, it is preferably 2 to 70% by mass based on the mass of the mixed solvent and more preferably 5 to 50% by mass. The solvent is preferably used in a homogeneous state, however, it may also be used in a heterogeneous state.

The liquid-phase oxidation may be carried out by any one of a continuous type operation and a batch type operation, however, a continuous type operation is industrially preferable in consideration of the productivity.

The amount of use of the olefin or the α,β-unsaturated aldehyde which is the raw material of the liquid-phase oxidation is preferably 0.1 to 20 parts by mass to 100 parts by mass of the solvent and more preferably 0.5 to 10 parts by mass.

The amount of use of the molecular oxygen is preferably 0.1 to 30 moles to 1 mole of the olefin or the α,β-unsaturated aldehyde which is the raw material, more preferably 0.3 to 25 moles and particularly preferably 0.5 to 20 moles.

Usually, the foregoing catalyst is used in a suspended state in the reaction liquid in which the liquid-phase oxidation is carried out, however, it may also be used in a fixed bed. The amount of use of the foregoing catalyst is preferably 0.1 to 30 parts by mass as the catalyst existing in the reactor to 100 parts by mass of the solution existing in the reactor, more preferably 0.5 to 20 parts by mass and particularly preferably 1 to 15 parts by mass.

The reaction temperature and the reaction pressure are properly selected according to the solvent and the raw material for the reaction to be used. The reaction temperature is preferably 30 to 200° C. and more preferably 50 to 150° C. The reaction pressure is preferably from the atmospheric pressure (0 MPa) to 10 MPa and more preferably 2 to 7 MPa.

EXAMPLES

Hereinafter, the present invention will be more concretely explained by way of examples and comparative examples, however, the present invention is not limited to these examples. The term "part(s)" in the following examples and comparative examples means part(s) by mass.
(Analyses of Raw Materials and Products)

Analyses of raw materials and products were carried out with gas chromatography. The conversion of an olefin or an α,β-unsaturated aldehyde, the selectivity to an α,β-unsaturated aldehyde to be produced and the selectivity to an α,β-unsaturated carboxylic acid to be produced are defined as follows:

Conversion of an olefin or an α,β-unsaturated aldehyde (%)=(B/A)×100

Selectivity to an α,β-unsaturated aldehyde (%)=(C/B)×100

Selectivity to an α,β-unsaturated carboxylic acid (%)=(D/B)×100

In these formulae, A represents mole number of an olefin or an α,β-unsaturated aldehyde supplied, B represents mole number of an olefin or an α,β-unsaturated aldehyde reacted, C represents mole number of an α,β-unsaturated aldehyde produced and D represents mole number of an α,β-unsaturated carboxylic acid produced. Now, in the case of an oxidation reaction of an α,β-unsaturated aldehyde, C/B is 0.

Now, the following examples and comparative examples deal with reactions of producing methacrylic acid from isobutylene, and in these cases, A represents mole number of isobutylene supplied, B represents mole number of isobutylene reacted, C represents mole number of methacrolein produced and D represents mole number of methacrylic acid produced.

Example 1

Catalyst Preparation

In 20.0 parts of acetic acid, 2.2 parts of palladium(II) acetate (manufactured by N. E. Chemcat Corporation, thermal decomposition temperature: 230° C.) was dissolved to prepare an acetic acid solution. To 20.0 parts of a silica carrier (specific surface area. 450 m$^2$/g; pore volume: 0.68 cc/g), the foregoing acetic acid solution was added little by little and shaken while these operations were repeated. When once the amount of the acetic acid solution equivalent to the total pore volume of the silica carrier was added, evaporation of the system was carried out. The remainder of the acetic acid solution was treated in the same way, namely, added little by little and shaken while these operations were repeated and finally, evaporation of the system was carried out to obtain the silica carrier on which palladium(II) acetate was supported. Thereafter, the silica carrier on which palladium (II) acetate was supported was homogeneously spread in a stainless steel vat (15 cm×20 cm) to a thin layer, and was subjected to a heat treatment of raising the temperature from a room temperature to 450° C. in air at a rate of 2.5° C./min, keeping the temperature at 450° C. for 3 hours and lowering the temperature to the room temperature. XRD measurement of the catalyst precursor thus obtained was carried out and formation of palladium oxide was confirmed.

The resultant catalyst precursor was added to 50.0 parts of 37% by mass formaldehyde aqueous solution. Then the system was heated to 70° C., kept at 70° C. for 2 hours while stirred, filtrated under reduced pressure and filtrated while washed with 1,000 parts of pure water. Further, the resultant system was dried at 100° C. for 2 hours under nitrogen flow to obtain 21 parts of a palladium-containing supported catalyst (loading ratio of palladium metal: 5.0% by mass). XRD measurement of the catalyst thus obtained was carried out and it was confirmed that the XRD peaks originating from palladium oxide disappeared and palladium metal was formed.
(Evaluation of Reaction)

Half the amount of the catalyst obtained by the foregoing method was filtrated while washed with 75% by mass t-butanol aqueous solution. The catalyst thus obtained and 75 parts of 75% by mass t-butanol aqueous solution as a reaction solvent were introduced into an autoclave and the autoclave was shut tight. Subsequently, 2.0 parts of isobutylene was introduced into it, and the stirring of the system (number of revolutions: 1,000 rpm) was started and the system was heated to 90° C. After the heating was finished, nitrogen was introduced into the autoclave to the internal pressure of 2.4 MPa and then compressed air was introduced into it to the internal pressure of 4.8 MPa. When the internal pressure dropped by 0.1 MPa (the internal pressure: 4.7 MPa) during the reaction, oxygen was introduced into it by 0.1 MPa, and this operation was repeated. The internal pressure right after the oxygen introduction was 4.8 MPa. The reaction was finished 30 minutes after the start of the reaction.

After the reaction was finished, the inside of the autoclave was cooled by ice bath. A gas-collecting bag was attached to the gas outlet of the autoclave and the gas outlet was opened and the emerging gas was collected while the internal pressure of the reactor was released. The reaction liquid containing catalyst was taken out from the autoclave and the catalyst was separated with membrane filter and the reaction liquid was recovered. The recovered reaction liquid and the collected gas were analyzed with gas chromatography, and the conversion and selectivity were calculated.

Example 2

Catalyst Preparation

The same procedure as in Example 1 was carried out except that a heat treatment of raising the temperature to 300° C. at a rate of 2.5° C./min and keeping the temperature at 300° C. for 3 hours was carried out. Now, XRD measurement of the catalyst precursor was carried out and formation of palladium oxide was confirmed. Further, in the palladium-containing supported catalyst thus obtained (loading ratio of palladium metal: 5.0% by mass), it was confirmed that the XRD peaks originating from palladium oxide disappeared and palladium metal was formed.

(Evaluation of Reaction)
The same procedure as in Example 1 was carried out.

Example 3

Catalyst Preparation

The same procedure as in Example 1 was carried out except that a heat treatment of raising the temperature to 600° C. at a rate of 2.5° C./min and keeping the temperature at 600° C. for 3 hours was carried out. Now, XRD measurement of the catalyst precursor was carried out and formation of palladium oxide was confirmed. Further, in the palladium-containing supported catalyst thus obtained (loading ratio of palladium metal: 5.0% by mass), it was confirmed that the XRD peaks originating from palladium oxide disappeared and palladium metal was formed.
(Evaluation of Reaction)
The same procedure as in Example 1 was carried out.

Example 4

Catalyst Preparation

In 22.0 g of palladium(II) nitrate solution (manufactured by Sigma-Aldrich Corporation, a solution containing 10% by mass of palladium(II) nitrate in 10% by mass nitric acid aqueous solution, thermal decomposition temperature of palladium(II) nitrate: 120° C.), 20.0 parts of a silica carrier (specific surface area: 450 m$^2$/g; pore volume: 0.68 cc/g) was soaked and the resultant system was evaporated to obtain the silica carrier on which palladium(II) nitrate was supported. Thereafter, the silica carrier on which palladium(II) nitrate was supported was homogeneously spread in a stainless steel vat (15 cm×20 cm) to a thin layer, and was subjected to a heat treatment of raising the temperature from a room temperature to 450° C. in air at a rate of 2.5° C./min, keeping the temperature at 450° C. for 3 hours and lowering the temperature to the room temperature. XRD measurement of the catalyst precursor thus obtained was carried out and formation of palladium oxide was confirmed.

The resultant catalyst precursor was added to 50.0 parts of 37% by mass formaldehyde aqueous solution. Then the system was heated to 70° C., kept at 70° C. for 2 hours while stirred, filtrated under reduced pressure and filtrated while washed with 1,000 parts of pure water. Further, the resultant system was dried at 100° C. for 2 hours under nitrogen flow to obtain a palladium-containing supported catalyst (loading ratio of palladium metal: 5.0% by mass). XRD measurement of the catalyst thus obtained was carried out and it was confirmed that the XRD peaks originating from palladium oxide disappeared and palladium metal was formed.
(Evaluation of Reaction)
The same procedure as in Example 1 was carried out.

Example 5

Catalyst Preparation

In 13.6 parts of pure water 2.8 parts of tetraamminepalladium(II) nitrate (manufactured by N. E. Chemcat Corporation, thermal decomposition temperature: 220° C.) was dissolved to prepare an aqueous solution. To 20.0 parts of a silica carrier (specific surface area, 450 m$^2$/g; pore volume: 0.68 cc/g), the foregoing aqueous solution was added little by little and shaken while these operations were repeated, and thereafter, evaporation of the system was carried out to obtain the silica carrier on which tetraamminepalladium(II) nitrate was supported. Thereafter, the silica carrier on which tetraamminepalladium(II) nitrate was supported was homogeneously spread in a stainless steel vat (15 cm×20 cm) to a thin layer, and was subjected to a heat treatment of raising the temperature from a room temperature to 450° C. in air at a rate of 2.5° C./min, keeping the temperature at 450° C. for 3 hours and lowering the temperature to the room temperature. XRD measurement of the catalyst precursor thus obtained was carried out and formation of palladium oxide was confirmed.

The resultant catalyst precursor was added to 50.0 parts of 37% by mass formaldehyde aqueous solution. Then the system was heated to 70° C., kept at 70° C. for 2 hours while stirred, filtrated under reduced pressure and filtrated while washed with 1,000 parts of pure water. Further, the resultant system was dried at 100° C. for 2 hours under nitrogen flow to obtain a palladium-containing supported catalyst (loading ratio of palladium metal: 5.0% by mass). XRD measurement of the catalyst thus obtained was carried out and it was confirmed that the XRD peaks originating from palladium oxide disappeared and palladium metal was formed.
(Evaluation of Reaction)
The same procedure as in Example 1 was carried out.

Example 6

Catalyst Preparation

In 140 parts of benzene, 2.8 parts of bis-(acetylacetonato)palladium(II) (manufactured by Sigma-Aldrich Corporation, thermal decomposition temperature: 210° C.) was dissolved to prepare a solution. In the foregoing benzene solution, 20.0 parts of a silica carrier (specific surface area: 450 m$^2$/g; pore volume, 0.68 cc/g) was soaked and the resultant system was evaporated to obtain the silica carrier on which bis-(acetylacetonato)palladium(II) was supported. Thereafter, the silica carrier on which bis-(acetylacetonato)palladium(II) was supported was homogeneously spread in a stainless steel vat (15 cm×20 cm) to a thin layer, and was subjected to a heat treatment of raising the temperature from a room temperature to 450° C. in air at a rate of 2.5° C./min, keeping the temperature at 450° C. for 3 hours and lowering the temperature to the room temperature. XRD measurement of the catalyst precursor thus obtained was carried out and formation of palladium oxide was confirmed.

The resultant catalyst precursor was added to 50.0 parts of 37% by mass formaldehyde aqueous solution. Then the system was heated to 70° C., kept at 70° C. for 2 hours while stirred, filtrated under reduced pressure and filtrated while washed with 1,000 parts of pure water. Further, the resultant system was dried at 100° C. for 2 hours under nitrogen flow to obtain a palladium-containing supported catalyst (loading ratio of palladium metal: 5.0% by mass). XRD measurement of the catalyst thus obtained was carried out and it was confirmed that the XRD peaks originating from palladium oxide disappeared and palladium metal was formed.
(Evaluation of Reaction)
The same procedure as in Example 1 was carried out.

Example 7

Catalyst Preparation

In 13.6 parts of 1N hydrochloric acid, 1.66 parts of palladium(II) chloride (manufactured by N. E. Chemcat Corporation, thermal decomposition temperature: 650° C.) was dissolved to prepare a solution. To 20.0 parts of a silica carrier (specific surface area: 450 m²/g; pore volume: 0.68 cc/g), the foregoing solution was added little by little and shaken while these operations were repeated, and thereafter, evaporation of the system was carried out to obtain the silica carrier on which palladium(II) chloride was supported. Thereafter, the silica carrier on which palladium(II) chloride was supported was homogeneously spread in a stainless steel vat (15 cm×20 cm) to a thin layer, and was subjected to a heat treatment of raising the temperature from a room temperature to 700° C. in air at a rate of 25° C./min, keeping the temperature at 700° C. for 3 hours and lowering the temperature to the room temperature. XRD measurement of the catalyst precursor thus obtained was carried out and formation of palladium oxide was confirmed.

The resultant catalyst precursor was added to 50.0 parts of 37% by mass formaldehyde aqueous solution. Then the system was heated to 70° C., kept at 70° C. for 2 hours while stirred, filtrated under reduced pressure and filtrated while washed with 1,000 parts of pure water. Further, the resultant system was dried at 100° C. for 2 hours under nitrogen flow to obtain a palladium-containing supported catalyst (loading ratio of palladium metal: 5.0% by mass). XRD measurement of the catalyst thus obtained was carried out and it was confirmed that the XRD peaks originating from palladium oxide disappeared and palladium metal was formed.

(Evaluation of Reaction)

The same procedure as in Example 1 was carried out.

Example 8

Catalyst Preparation

The same procedure as in Example 1 was carried out except that the silica carrier on which palladium(II) acetate was supported was introduced into a tall beaker and subjected to the heat treatment (the height of the silica carrier layer at the time of the heat treatment: about 5.0 cm).

(Evaluation of Reaction)

The same procedure as in Example 1 was carried out.

Example 9

Catalyst Preparation

The same procedure as in Example 4 was carried out except that the silica carrier on which palladium(II) nitrate was supported was introduced into a tall beaker and subjected to the heat treatment (the height of the silica carrier layer at the time of the heat treatment: about 5.0 cm).

(Evaluation of Reaction)

The same procedure as in Example 1 was carried out.

Comparative Example 1

Catalyst Preparation

The same procedure as in Example 7 was carried out except that a heat treatment of raising the temperature to 400° C. at a rate of 2.5° C./min and keeping the temperature at 400° C. for 3 hours was carried out. Now, XRD measurement of the catalyst precursor was carried out and it was found that palladium oxide was not formed. Further, in the palladium-containing supported catalyst thus obtained (loading ratio of palladium metal: 5.0% by mass), it was confirmed that palladium metal was formed.

(Evaluation of Reaction)

The same procedure as in Example 1 was carried out.

Comparative Example 2

Catalyst Preparation

The same procedure as in Example 1 was carried out except that a heat treatment of raising the temperature to 100° C. at a rate of 2.5° C./min, keeping the temperature at 100° C. for 3 hours was carried out. Now, XRD measurement of the solid obtained by the heat treatment was carried out and it was found that palladium oxide was not formed. Further, in the palladium-containing supported catalyst thus obtained (loading ratio of palladium metal: 5.0% by mass), it was confirmed that palladium metal was formed.

(Evaluation of Reaction)

The same procedure as in Example 1 was carried out.

Comparative Example 3

Catalyst Preparation

In 120 parts of 85% by mass acetic acid aqueous solution, 2.2 parts of palladium acetate was dissolved while heated to 80° C., and introduced into an autoclave together with 20.0 parts of a silica carrier (specific surface area: 450 m²/g; pore volume: 0.68 cc/g) and the autoclave was shut tight. The stirring of the system at 500 rpm was started and nitrogen gas was introduced into it to 0.8 MPa and this operation was repeated 3 times to replace the inside of the system with nitrogen. Thereafter propylene was introduced into it from the atmospheric pressure to 0.6 MPa and the system was heated to 70° C. and kept at the same temperature for 1 hour.

After the system was cooled to a room temperature, the internal pressure of the autoclave was released and the autoclave was opened. The resultant system was filtrated under reduced pressure and filtrated while washed with 1,000 parts of pure water. The resultant system was dried at 100° C. for 2 hours under nitrogen flow to obtain a palladium-containing supported catalyst (loading ratio of palladium metal: 5.0% by mass). XRD measurement of the catalyst thus obtained was carried out and it was confirmed that palladium metal was formed.

(Evaluation of Reaction)

The same procedure as in Example 1 was carried out.

TABLE 1

| | Pd Salts | | Heat | Conversion | Selectivity | Selectivity |
| | Kind | Thermal decomposition temp. (° C.) | treatment temp. (° C.) | of isobutylene (%) | to methacrolein (%) | to methacrylic acid (%) |
|---|---|---|---|---|---|---|
| Ex. 1 | Palladium(II) acetate | 230 | 450 | 41.5 | 42.1 | 40.9 |
| Ex. 2 | Palladium(II) acetate | 230 | 300 | 42.1 | 38.8 | 37.6 |

TABLE 1-continued

| | Pd Salts | | Heat treatment temp. (° C.) | Conversion of isobutylene (%) | Selectivity to methacrolein (%) | Selectivity to methacrylic acid (%) |
|---|---|---|---|---|---|---|
| | Kind | Thermal decomposition temp. (° C.) | | | | |
| Ex. 3 | Palladium(II) acetate | 230 | 600 | 37.1 | 42.6 | 42.4 |
| Ex. 4 | Palladium(II) nitrate | 120 | 450 | 43.0 | 43.9 | 40.6 |
| Ex. 5 | Tetraamminepalladium(II) nitrate | 220 | 450 | 41.3 | 43.6 | 42.4 |
| Ex. 6 | Bis-(acetylacetonato)palladium(II) | 210 | 450 | 42.3 | 40.5 | 42.9 |
| Ex. 7 | Palladium(II) chloride | 650 | 700 | 41.0 | 54.7 | 30.5 |
| Ex. 8 | Palladium(II) acetate | 230 | 450 | 28.6 | 59.3 | 26.5 |
| Ex. 9 | Palladium(II) nitrate | 120 | 450 | 45.3 | 45.1 | 40.7 |
| Comp. Ex. 1 | Palladium(II) chloride | 650 | 400 | 11.2 | 75.8 | 10.4 |
| Comp. Ex. 2 | Palladium(II) acetate | 230 | 100 | 24.6 | 68.5 | 20.7 |
| Comp. Ex. 3 | Palladium(II) acetate | 230 | no treatment | 15.4 | 75.0 | 11.4 |

As mentioned above, it was found that an α,β-unsaturated carboxylic acid can be produced in higher selectivity according to the present invention.

What is claimed is:

1. A method for producing an α,β-unsaturated carboxylic acid, comprising
   supporting a palladium salt on a carrier;
   heat treating said palladium salt present on said carrier to oxidize at least a part of said palladium salt to produce a catalyst precursor on said carrier that comprises palladium oxide, wherein said heat treating is carried out at a temperature of at least the thermal decomposition temperature of said palladium salt;
   reducing palladium oxide present in the catalyst precursor to produce a palladium containing supported catalyst; and
   liquid-phase oxidizing an olefin or an α,β-unsaturated aldehyde with molecular oxygen in the presence of the palladium-containing supported catalyst to produce an α,β-unsaturated carboxylic acid.

2. The method according to claim 1, wherein said thermal decomposition temperature of said palladium salt is 400° C. or lower.

3. The method according to claim 1, wherein said thermal decomposition temperature of said palladium salt is 300° C. or lower.

4. The method according to claim 1, wherein said thermal decomposition temperature of said palladium salt is 200° C. or lower.

5. The method according to claim 1, wherein said palladium salt has a thermal decomposition temperature of from 120 to 650° C.

6. The method according to claim 1, wherein said palladium salt comprises at least one member selected from the group consisting of palladium(II) chloride; palladium(II) acetate; palladium(II) nitrate; tetraamminepalladium(II) nitrate; and bis-(acetylacetonato)palladium(II).

7. The method according to claim 1, wherein said palladium salt comprises at least one member selected from the group consisting of palladium(II) acetate; palladium(II) nitrate; tetraamminepalladium(II) nitrate; and bis-(acetylacetonato)palladium(II).

8. The method according to claim 1, wherein said reducing palladium oxide present in the catalyst precursor comprises contacting said palladium oxide with a reducing agent that comprises at least one member selected from the group consisting of hydrazine, formaldehyde; sodium boron hydride; hydrogen; formic acid; formate; ethylene; propylene; 1-butene; 2-butene; isobutylene; 1,3-butadiene; 1-heptene; 2-heptene; 1-hexene; 2-hexene; cyclohexene; allylalcohol; methallyl alcohol; acrolein; and methacrolein.

9. The method according to claim 1, wherein said reducing palladium oxide present in the catalyst precursor comprises contacting said palladium oxide with gaseous hydrogen.

10. The method according to claim 1, wherein said reducing palladium oxide present in the catalyst precursor comprises contacting said palladium oxide with at least one of hydrazine, formaldehyde, formic acid, and formate, present in a liquid phase, and wherein said contacting is a liquid phase reaction.

11. The method according to claim 1, wherein said palladium-containing supported catalyst comprises at least 50% by mass of palladium, relative to the total mass of the catalyst, and further comprises at least one metal selected from the group consisting of ruthenium, rhodium, silver, osmium, iridium, platinum, gold, copper, antimony, tellurium, lead, and bismuth.

12. The method according to claim 1, wherein
   said olefin comprises at least one member selected from the group consisting of propylene, isobutylene, and 2-butene; and
   said an α,β-unsaturated aldehyde comprises at least one member selected from the group consisting of acrolein, methacrolein, crotonaldehyde and cinnamaldehyde.

13. The method according to claim 1, wherein said olefin or α,β-unsaturated aldehyde is present in a solution during said liquid phase oxidizing and present in said solution in an amount of from 0.1 to 20 parts by mass to 100 parts by mass of solvent.

14. The method according to claim 1, wherein a molar ratio of said molecular oxygen to said olefin or α,β-unsaturated aldehyde is from 0.1: to 30:1.

15. The method according to claim 1, wherein said olefin is propylene, said α,β-unsaturated aldehyde is acrolein and said α,β-unsaturated carboxylic acid is acrylic acid.

16. The method according to claim 1, wherein said olefin is isobutylene, said α,β-unsaturated aldehyde is methacrolein and said α,β-unsaturated carboxylic acid is methacrylic acid.

17. The method according to claim 1, wherein said liquid-phase oxidizing is carried out a temperature of from 30 to 200° C.

18. The method according to claim 1, wherein said liquid-phase oxidizing is carried out a temperature of from 50 to 150° C.

19. The method according to claim 1, wherein said liquid-phase oxidizing is carried out a pressure of atmospheric pressure to 10 MPa.

20. The method according to claim 1, wherein said olefin or said α,β-unsaturated aldehyde and said palladium-containing supported catalyst are present in a solution, and said palladium-containing supported catalyst is present in said solution in an amount of from 0.1 to 30 parts by mass, relative to 100 parts by mass of said solution.

* * * * *